(12) United States Patent
Tarniceriu et al.

(10) Patent No.: US 11,844,594 B2
(45) Date of Patent: Dec. 19, 2023

(54) METHOD, AN APPARATUS AND A COMPUTER PROGRAM PRODUCT FOR ESTIMATING THE QUALITY OF A SIGNAL

(71) Applicant: PulseOn Oy, Espoo (FI)

(72) Inventors: Adrian Tarniceriu, Zurich (CH); Zeinab Rezaeiyousefi, Espoo (FI); Jakub Parak, Jyväskylä (FI)

(73) Assignee: Pulseon OY, Espoo (FI)

( * ) Notice: Subject to any disclaimer, the term of this patent is extended or adjusted under 35 U.S.C. 154(b) by 346 days.

(21) Appl. No.: 17/054,249

(22) PCT Filed: May 13, 2019

(86) PCT No.: PCT/FI2019/050377
§ 371 (c)(1),
(2) Date: Nov. 10, 2020

(87) PCT Pub. No.: WO2019/220012
PCT Pub. Date: Nov. 21, 2019

(65) Prior Publication Data
US 2021/0068687 A1  Mar. 11, 2021

(30) Foreign Application Priority Data
May 14, 2018 (FI) ...................................... 20185441

(51) Int. Cl.
*A61B 5/00* (2006.01)
*A61B 5/024* (2006.01)
(Continued)

(52) U.S. Cl.
CPC ...... *A61B 5/02416* (2013.01); *A61B 5/02405* (2013.01); *A61B 5/02438* (2013.01);
(Continued)

(58) Field of Classification Search
CPC ............ A61B 5/02416; A61B 5/14551; A61B 5/02405; A61B 5/02438; A61B 5/681;
(Continued)

(56) References Cited

U.S. PATENT DOCUMENTS

| 9,357,937 B2 | 6/2016 | Watson et al. |
| 2014/0066785 A1 | 3/2014 | Watson et al. |

(Continued)

FOREIGN PATENT DOCUMENTS

| WO | 2017142667 A1 | 8/2017 |
| WO | 2018005729 A1 | 1/2018 |

OTHER PUBLICATIONS

Karlen W et al: Paper; Photoplethysmogram signal quality estimation using repeated Gaussian filters and cross-correlation; Physiological Measurement, Institute of Physics Publishing, Bristol, GB, vol. 33, No. 10, Sep. 18, 2012 (Sep. 18, 2012-), pp. 1617-1629 (Year: 2012).*

(Continued)

*Primary Examiner* — Jeffrey P Aiello
(74) *Attorney, Agent, or Firm* — Thomas| Horstemeyer, LLP

(57) ABSTRACT

A method for estimating the quality of a signal comprising: receiving a periodic signal comprising a first wave and a second wave; estimating similarity between the first wave and the second wave; assigning a weight for the second wave based on the similarity between the first wave and the second wave; classifying the second wave as non-reliable when the weight fails to exceed a predefined threshold.

18 Claims, 9 Drawing Sheets

(51) Int. Cl.
  *G16H 40/67* (2018.01)
  *G16H 50/20* (2018.01)
  *G16H 50/70* (2018.01)
  *G01P 15/18* (2013.01)

(52) U.S. Cl.
  CPC .......... *A61B 5/6824* (2013.01); *A61B 5/6831* (2013.01); *A61B 5/7221* (2013.01); *A61B 5/7246* (2013.01); *A61B 5/7264* (2013.01); *G01P 15/18* (2013.01); *G16H 40/67* (2018.01); *G16H 50/20* (2018.01); *G16H 50/70* (2018.01); *A61B 2562/0219* (2013.01)

(58) Field of Classification Search
  CPC ... A61B 5/6824; A61B 5/6831; A61B 5/7221; A61B 5/7246; A61B 5/7264; G16H 40/67; G16H 50/20
  USPC ....... 340/539.12; 356/41; 600/301, 323–324, 600/509; 702/19, 57, 66, 70–74, 85, 141, 702/150, 179, 189–190; 703/11
  See application file for complete search history.

(56) References Cited

U.S. PATENT DOCUMENTS

| | | | |
|---|---|---|---|
| 2016/0302674 A1* | 10/2016 | Moyer | A61B 5/259 |
| 2016/0360984 A1* | 12/2016 | Albadawi | A61B 5/7246 |
| 2018/0000426 A1* | 1/2018 | Li | A61B 5/1102 |
| 2018/0177459 A1* | 6/2018 | Eletr | A61B 5/02125 |
| 2019/0282179 A1* | 9/2019 | Newberry | A61B 5/7275 |
| 2019/0328338 A1* | 10/2019 | Hu | A61B 5/02416 |
| 2020/0237317 A1* | 7/2020 | Newberry | A61B 5/1455 |
| 2021/0259557 A1* | 8/2021 | Frank | G01J 3/50 |
| 2021/0275034 A1* | 9/2021 | Frank | A61B 5/0075 |
| 2022/0225945 A1* | 7/2022 | Eletr | A61B 5/259 |

OTHER PUBLICATIONS

Karlen W et al: Paper; Photoplethysmogram signal quality estimation using repeated Gaussian filters and cross-correlation; Physiological Measurement, Institute of Physics Publishing, Bristol, GB, vol. 33, No. 10, Sep. 18, 2012 (Sep. 18, 2012), pp. 1617-1629, XP020230292, ISSN: 0967-3334: DOI: 10.1088/0967-3334/33/10/1617 section 2. Algorithm design; p. 1619-p. 1922.

Chetanya Puri et al: "iCarMa", Iot-Enabled Healthcare and Wellness Technologies and Systems, ACM, 2 Penn Plaza, Suite 701 New York NY 10121-0701, USA, Jun. 30, 2016 (Jun. 30, 2016), pp. 3-8, XP058260975, DOI: 10.1145/2933566.2933567, ISBN: 978-1-4503-4334-3, the whole document.

European Office Action for European Patent Application No. 19726461.7 dated Oct. 16, 2023.

* cited by examiner

FIG. 9A
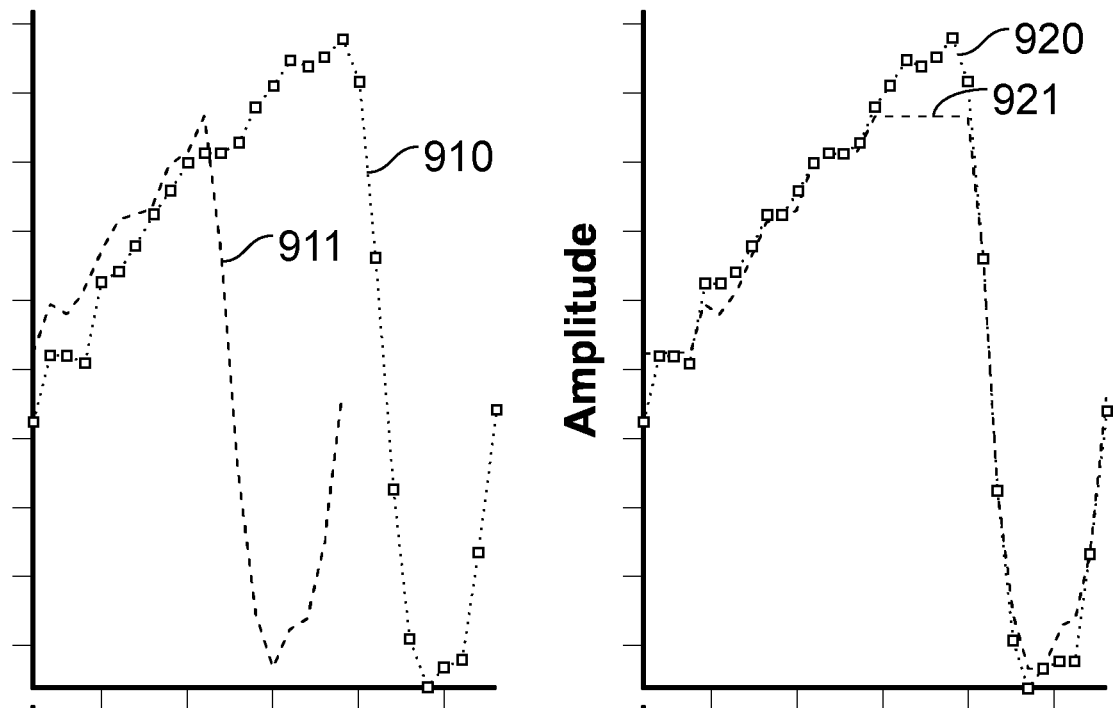
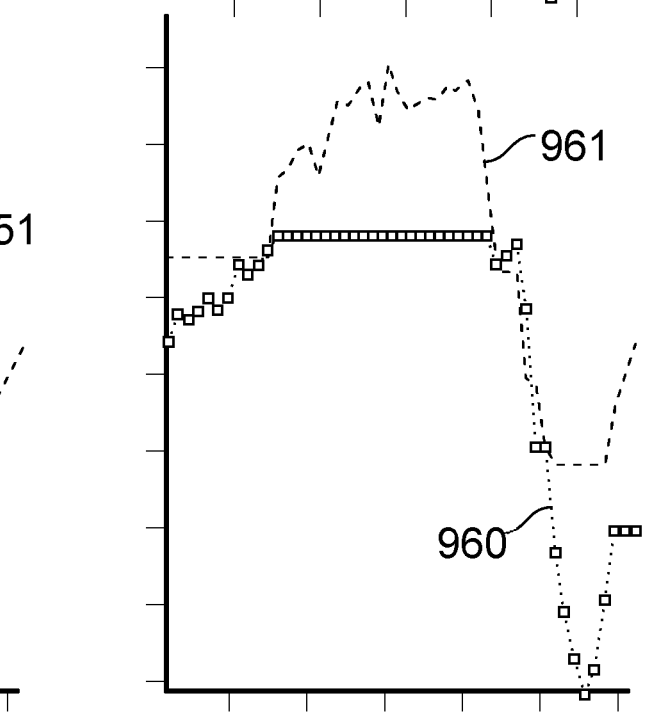
FIG. 9B

METHOD, AN APPARATUS AND A COMPUTER PROGRAM PRODUCT FOR ESTIMATING THE QUALITY OF A SIGNAL

PRIORITY

This application is a U.S. national application of the international application number PCT/FI2019/050377 filed on May 13, 2019, which claims priority of Finnish application FI20185441 filed on May 14, 2018, the contents of all of which are incorporated herein by reference.

TECHNICAL FIELD

Various example embodiments relate to the quality estimation of a periodic signal, e.g. photoplethysmogram signal.

BACKGROUND

Periodic signals originate often from physiological measurements. Examples of periodic or rhythmic signals comprise e.g. photoplethysmogram (PPG) signals, electrocardiogram (ECG) signals and respiration airflow signals.

Physiological data can be measured from a user by using biometric monitors, which may be attached to the user, for example to the chest, wrist, forearm, finger or arm of the user. The physiological data may include for example heart rate.

Quality and reliability of the periodic signals may be reduced for several reasons. Corruption of the signal reduces the accuracy of the parameters estimated from the signal.

There is, therefore, a need for a solution for estimating the reliability of the signal to improve the accuracy of the measurement.

SUMMARY

Now there has been invented a method and technical equipment implementing the method, by which the above problems are alleviated. Various aspects of the invention include a method, an apparatus, and a computer program product comprising computer program code stored therein, which are characterized by what is stated in the independent claims. Various example embodiments are disclosed in the dependent claims.

According to a first aspect, there is provided a method for estimating the quality of a signal, the method comprising receiving a periodic signal comprising a first wave and a second wave; estimating similarity between the first wave and the second wave; assigning a weight for the second wave based on the similarity between the first wave and the second wave; classifying the second wave as non-reliable when the weight fails to exceed a predefined threshold.

According to an embodiment, the first and the second waves are consecutive waves.

According to an embodiment, the signal is a photoplethysmogram (PPG) signal comprising a first PPG wave and a second PPG wave.

According to an embodiment, the method further comprises determining the derivative of the PPG signal.

According to an embodiment, the method further comprises determining an inter-beat interval (IBI) for the second PPG wave.

According to an embodiment, the estimating similarity comprises determining a normalized first wave and a normalized second wave; determining warped versions of the normalized first and the second waves; determining a correlation coefficient between the warped versions of the normalized first and the second waves; classifying the second wave as non-reliable if the correlation coefficient fails to exceed a predefined threshold.

According to an embodiment, the method further comprises receiving accelerometer signal; classifying the waves based on the accelerometer signal, the classifying comprising determining beat motion level based on the accelerometer signal; classifying the waves as non-reliable if the beat motion level exceeds a predefined threshold.

According to an embodiment, the method further comprises classifying one or more beats following the non-reliable wave as non-reliable.

According to an embodiment, the method further comprises assigning the weight based on a distance of the similarity from the threshold, wherein the weight is obtained by subtracting a multiple of the distance from 1.

According to an embodiment, the method further comprises discarding the second wave as non-reliable when the weight is zero or negative.

According to a second aspect, there is provided an apparatus comprising means for receiving a periodic signal comprising a first wave and a second wave; estimating similarity between the first wave and the second wave; assigning a weight for the second wave based on the similarity between the first wave and the second wave; classifying the second wave as non-reliable when the weight fails to exceed a predefined threshold.

According to an embodiment, the apparatus is a monitoring device comprising an optical sensor for measuring photoplethysmogram (PPG) signals.

According to an embodiment, the means comprise at least one processor; at least one memory including computer program code; the at least one memory and the computer program code configured to, with the at least one processor, cause the performance of the apparatus.

According to a third aspect, there is provided a computer program comprising computer program code configured to, when executed on at least one processor, cause an apparatus to carry out the method according to various embodiments.

DESCRIPTION OF THE DRAWINGS

In the following, various example embodiments will be described in more detail with reference to the appended drawings, in which

FIG. 9a shows, by way of an example, original signals and warped signals using DTW; and FIG. 9b shows, by way of an example, original signals and warped signals using DTW.

Drawings are schematic.

DESCRIPTION OF EXAMPLE EMBODIMENTS

In the following, several example embodiments will be described in the context of photoplethysmography (PPG) signal. It is to be noted, however, that the invention is not limited to PPG. In fact, the different embodiments have applications in any environment where quality of a periodic signal needs to be estimated. Examples of periodic or rhythmic signals comprise e.g. electrocardiogram (ECG) signals and respiration airflow signals.

Physiological data can be measured from a user by using biometric monitors, such as portable and/or wearable biometric monitors, which may be attached to the user, for example to the chest, wrist, forearm, finger or arm of the user. The physiological data may include for example heart rate. Such biometric monitors, which may be attached to a user for example with a strap, tend to move when the user moves resulting in an unstable contact of the sensor of the monitoring device with the user's skin. This may corrupt the signal measured with the sensor, so especially signals measured with portable and/or wearable monitoring devices need to be estimated for their reliability.

One way for measuring the heart rate is using optical measurement. The optical heart rate measurement is based on the fact that light is emitted by one or more light sources towards body tissue and at least one detector is configured to detect the intensity of reflected or back-scattered light after propagation through the body tissue. This technique is called photoplethysmography (PPG).

With each cardiac cycle the heart pumps blood to the periphery. This causes changes in the blood volume in the subcutaneous tissue and skin capillaries. The change in volume caused by the pressure pulse may be detected for example by illuminating the skin with the light from a light-emitting diode (LED) and then measuring the amount of light either transmitted or reflected to a photodiode. Each cardiac cycle appears as a downward peak in the photodiode current. Because blood flow to the skin can be modulated by multiple other physiological systems, the photoplethysmography can also be used to monitor breathing, hypovolemia, and other circulatory conditions.

Raw PPG signals are often corrupted by noise caused by subject motion, imperfect contact between the skin and the biometric monitor, ambient light conditions, or other. Additionally, the shape of the PPG waveform differs from subject to subject, and varies with the location and manner in which the pulse oximeter is attached. Even if some of these interferences can be filtered out, they reduce quality and reliability of the PPG signal and therefore reduce the accuracy of the measurement. Detection of beat-to-beat intervals is especially sensitive to such interferences.

Figure 1A:
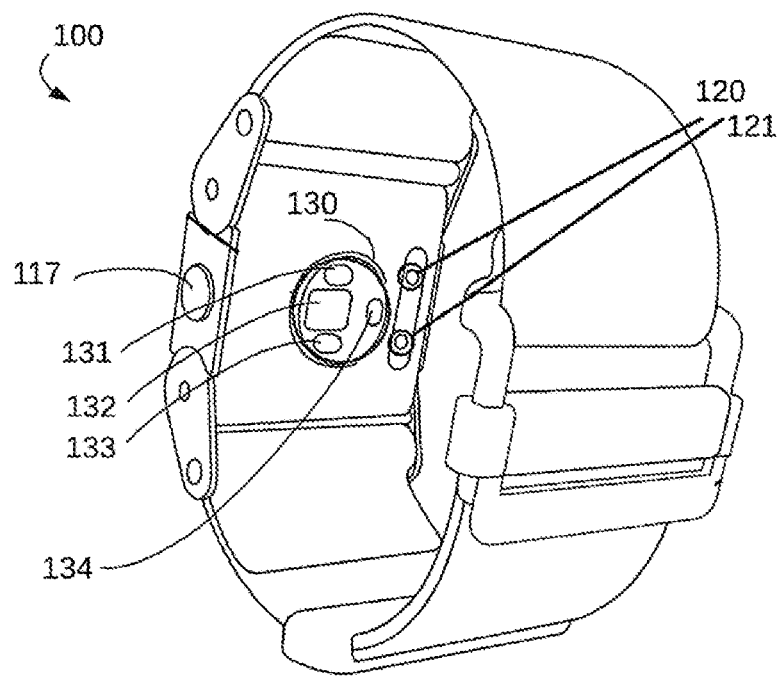
FIGS. 1a and 1b show, by way of examples, a monitoring device for measuring photoplethysmography signals.
Figure 1B:
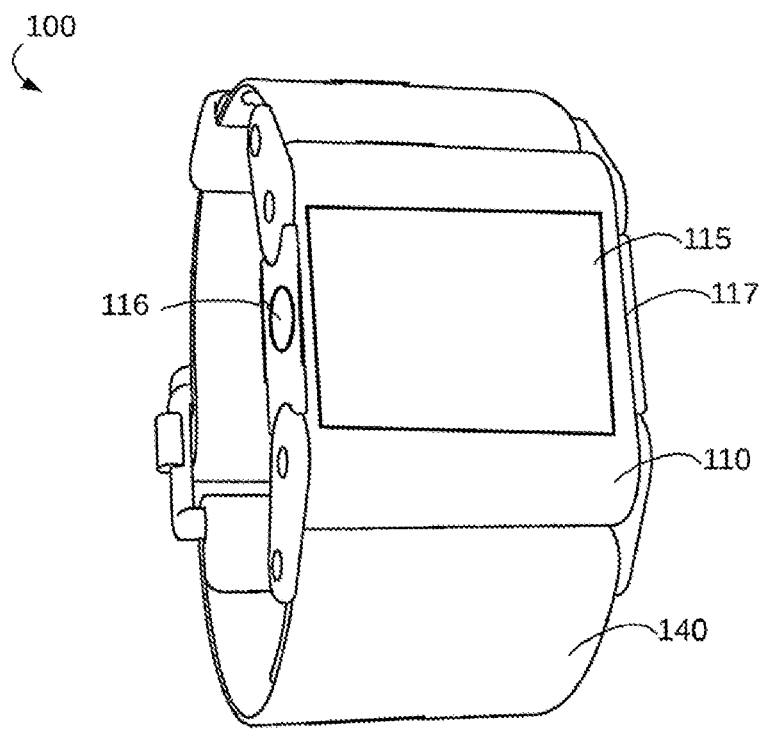

FIGS. 1a and 1b show, by way of an example, a portable monitoring device 100 for measuring a photoplethysmogram (PPG) signal. The monitoring device for measuring PPG comprises an optical sensor 130. The optical sensor comprises a light source 131, 133, 134 illuminating the skin of a user and a photodetector 132 detecting the intensity of refracted light. The light source may be a green light emitting diode (LED) 131, 133 or infra-red (IR) LED 134. The LED illuminates the skin and the small capillary vessels close to it. The photodetector may be an electro-optical cell which detects the light which is back-scattered from the skin and tissue. When the heart pumps, the blood flow varies according to the heart's pumping frequency.

The monitoring device 100 further comprises charging connectors 120, 121. The monitoring device may comprise one or more buttons 117 for receiving input from the user.

As shown in FIG. 1b, the monitoring device comprises a casing 110. The casing comprises e.g. the optical sensor 130 and means such as circuitry and electronics for receiving the measured signal from the optical sensor and handling the signal data and user input received through the buttons 116, 117. Further, the casing may comprise electronics for e.g. navigation and timing. The casing comprises a screen 115. The screen displays information to the user. For example, the user may see parameters derived from the measured PPG signal on the screen, such as heart rate and inter-beat interval. Further, the current date and time may be displayed on the screen. The monitoring device comprises a strap 140 for attaching the device to the wrist of the user. There are also other options for attaching the optical sensor 130 to the user. For example in hospital environments, the optical sensor may be attached on the skin using e.g. a patch. As another example, the optical sensor may be integrated to a ring to be worn on a finger of a user. The measured signal may be transmitted via wired or wireless connection to a personal computer where it may be analysed further.

Figure 2A:
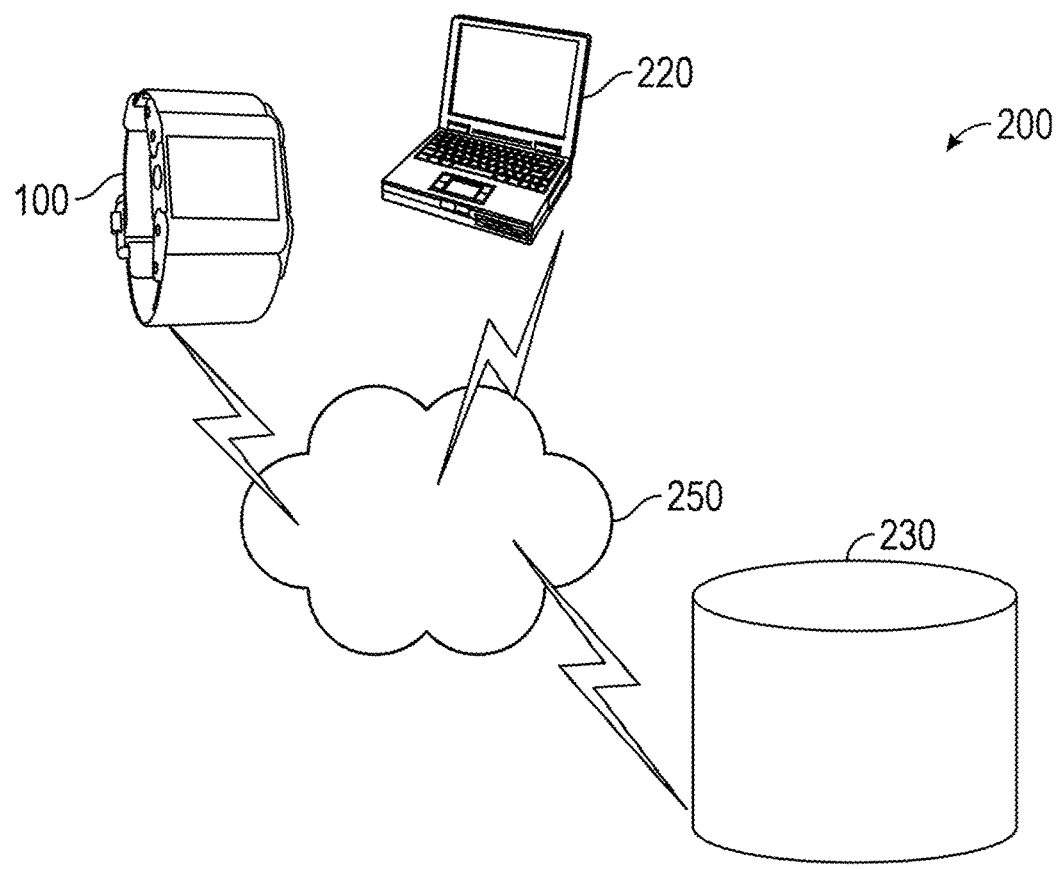
FIG. 2a shows, by way of an example, a system and devices for estimating quality of a signal.

FIG. 2a shows, by way of example, a system and devices for estimating quality of a signal. All processing could be done inside the monitoring device 100 or, alternatively, different devices may be connected to each other via a communication connection 250, e.g. vie Internet, a mobile communication network, Wireless Local Area Network (WLAN), Bluetooth, or other contemporary and future networks. Different networks may be connected to each other by means of a communication interface. Signals measured by the monitoring device 100 may be stored in the device 100 and/or in a database 230. The database may be a server or a group of servers. The servers may form a server system, e.g. a cloud. The monitoring device 100 may be connected to a user device 220 via wired or wireless connection. The user device may be e.g. a personal computer, a laptop or a smartphone. A user of the user device 220 may use a user interface of the user device for e.g. viewing and analyzing the measurements of the monitoring device 100 and enter e.g. personal settings to the monitoring device.

Figure 2B:
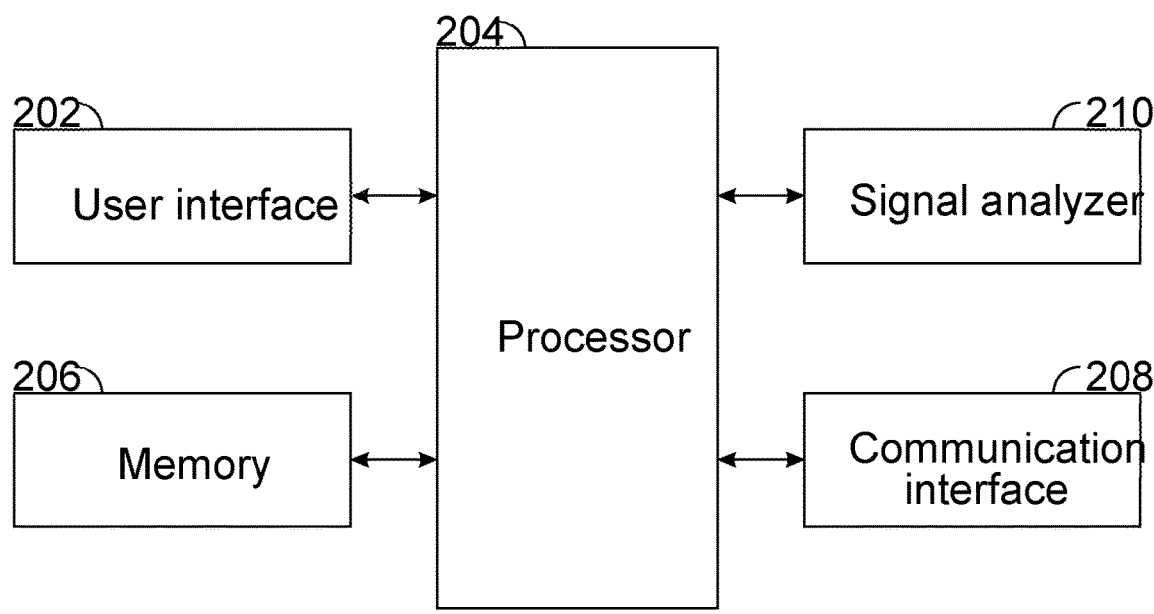
FIG. 2b shows, by way of an example, a block diagram of an apparatus.

FIG. 2b shows, by way of an example, a block diagram of an apparatus. The apparatus may be the monitoring device 100 and/or the server. The apparatus may receive user input such as commands, parameters etc. via a user interface 202 and/or via communication interface 208. The user interface may receive user input e.g. through buttons and/or a touch screen. Alternatively, the user interface may receive user input from internet or a personal computer or a smartphone via a communication connection. The communication connection may be e.g. a Bluetooth connection or a WiFi connection. The apparatus may comprise a memory 206 for storing data and computer program code which can be executed by a processor 204 to carry out various embodiment of the method as disclosed herein. A signal analyzer 210 may be configured to implement the elements of the method disclosed herein. The signal analyzer may receive the signal to be processed from the memory. The elements of the method may be implemented as a software component residing in the monitoring device. Alternatively, the elements of the method may be implemented as a software component residing in a server. The server may receive the signal to be processed e.g. from the monitoring device and store the signal in the memory. A computer program product may be embodied on a non-transitory computer readable medium.

Figure 3A:
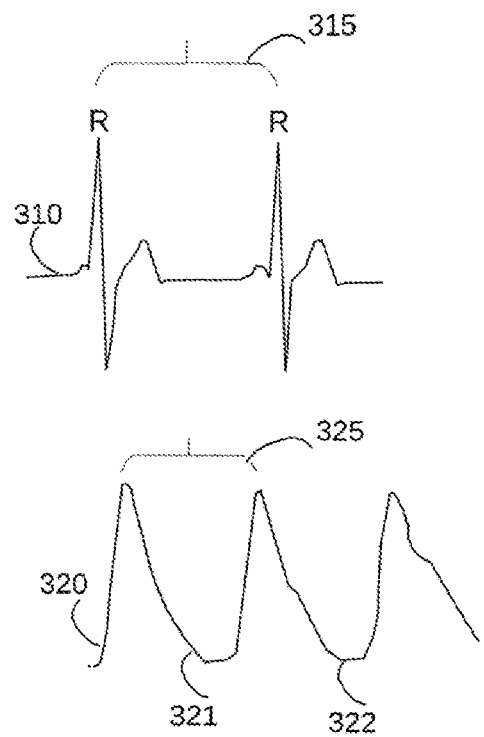
FIG. 3a shows, by way of an example, an electrocardiography signal and a photoplethysmogragphy signal.

FIG. 3a shows, by way of an example, an electrocardiogram (ECG) signal 310 and a photoplethysmography signal 320. Inter-beat interval (IBI) 325 is a time interval between heart beats, analogously to R-R interval 315 in ECG signal. The PPG signal 320 comprises PPG waves 321, 322. IBI may be computed for each wave. IBI is usually measured in units of milliseconds. IBI varies from beat to beat, and this natural variation is known as heart rate variability (HRV). HRV measures the changes in time between successive heart beats. A low HRV, i.e. less variability in the heart beats, indicates that the body of the user is under stress e.g. from exercise or psychological events. A high HRV, i.e. greater variability in the heart beats, indicates that the body is stress tolerant or is recovering from prior stress. Via HRV analysis, it is possible to gain knowledge of the function of the autonomic nervous system (ANS).

Figure 3B:
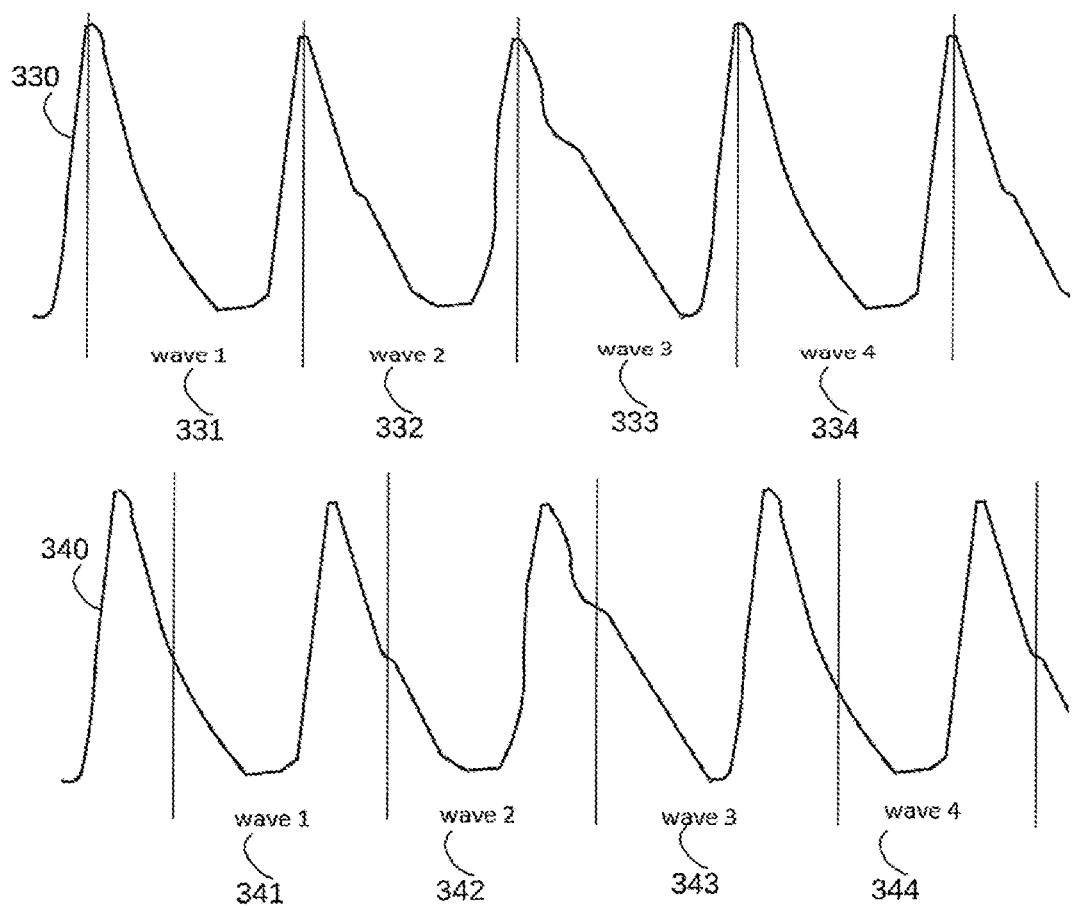
FIG. 3b shows, by way of an example, photoplethysmography signals.

FIG. 3b shows, by way of an example, photoplethysmography signals 330, 340. Waves of the PPG signal may be defined in different ways. IBI is the duration of one wave. Waves 331, 332, 333, 334 in the PPG signal 330 are defined between maximas of the PPG signal. IBI may be computed e.g. by computing the time intervals between two successive maxima of the PPG signal.

Waves 341, 342, 343, 344 in the PPG signal 340 are defined using the derivative of the PPG signal (dPPG). When using derivative of the PPG signal, IBI may be computed e.g. by computing the time intervals between two successive minima of the dPPG. Use of the dPPG instead of raw PPG signal may result in increased accuracy.

Computation of IBI is not reliable in the presence of noise. In the absence of noise, successive PPG waves are highly similar. Similarity of the successive PPG waves can assess the reliability of IBI calculations. PPG signal may be corrupted or noisy due to e.g. motion of the user, small movements of the monitoring device or of the optical sensor, with regard to the skin, varying ambient lighting conditions, or analog front-end changes. If there is noise, the likelihood of consecutive waves being similar is very low and the IBI calculations may be unreliable. Corruption of the signal reduces the accuracy of the parameters estimated from the signal, such as inter-beat interval and heart rate variability. HRV monitoring and arrhythmia detection are very sensitive to IBI errors. Therefore, identification of unreliable IBIs is important to be able to discard them from further signal processing and analysis.

Motion of the user may be measured by an accelerometer. The accelerometer may be a multi-axis accelerometer, e.g. a 3-axis accelerometer. Thus, when measuring PPG and acceleration at the same time, it is possible to detect the beats, i.e. waves, corrupted by motion based on the acceleration signal. The corrupted beats may be discarded from the IBI computation.

The motion level corresponding to each beat, or beat motion level, may be estimated from the acceleration signal. As example, some of the acceleration measures that could be used are:
- maximum acceleration value for each of the 3 axes, for each beat
- summation of absolute values of the acceleration in all 3 axes
- L2 norm of the 3 acceleration axes
- standard deviation of the L2 norm of the 3 acceleration axes
- smoothed norm of the acceleration signal.

The beat motion level may be determined based on the smoothed, band-passed L2 norm of the acceleration signal. If the beat motion level exceeds a pre-defined threshold, e.g., 0.05 g, 0.1 g, or other, wherein the g is the gravitational acceleration, the beat is classified as non-reliable. The non-reliable beat may be discarded from the IBI computation. In addition to the current non-reliable beat, one or more following beats may be classified as non-reliable. For example, four following beats may be discarded from the computation.

Figure 4:
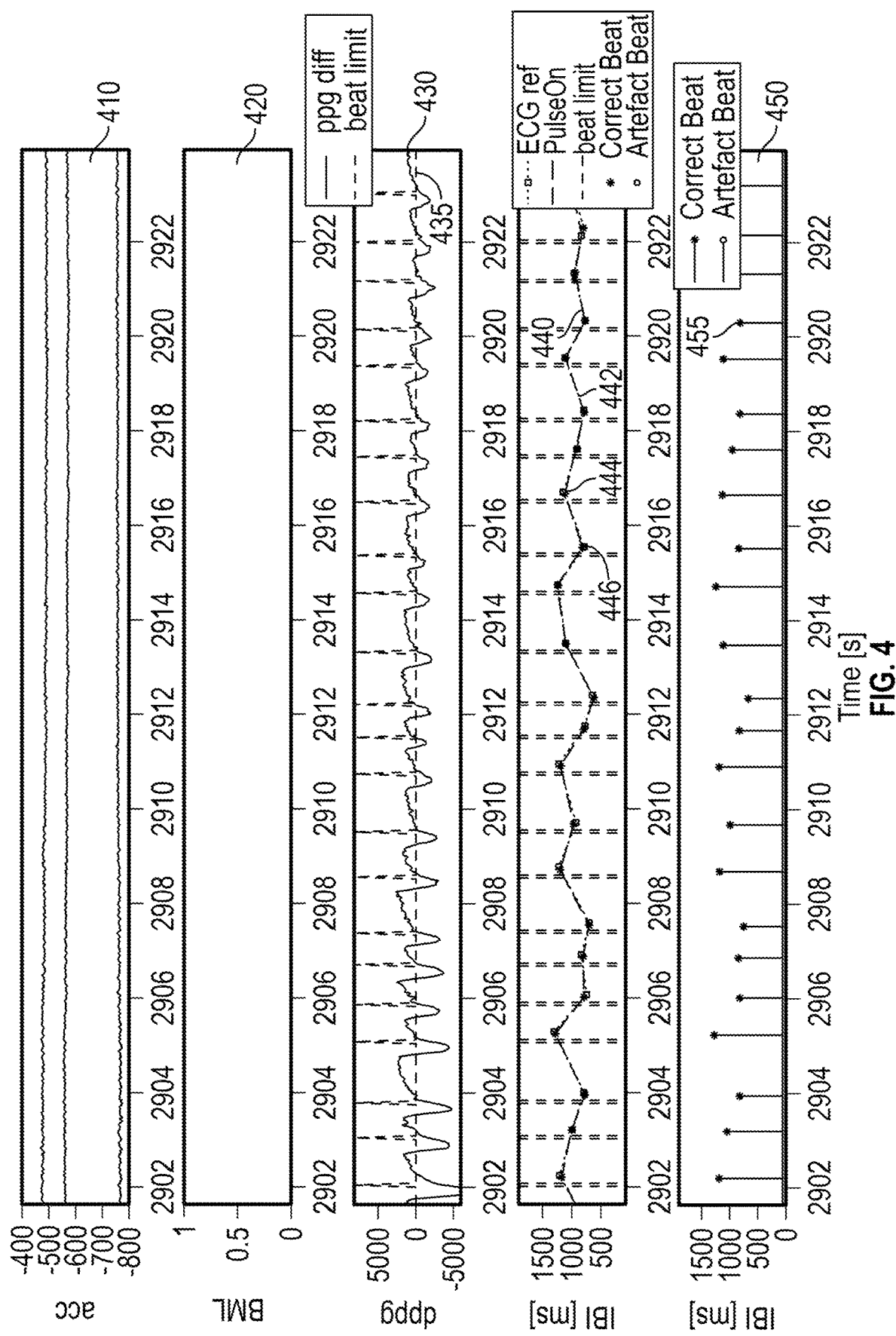
FIG. 4 shows examples of signals.

FIG. 4 shows examples of signals. The signal 410 is the acceleration signal. The signal 420 is a beat motion level that may be estimated from the acceleration signal. The signal 430 is the derivative of the PPG signal. The signal 435 is the beat limit as returned by the IBI estimation algorithm. IBIs are computed as the time-distance between consecutive local minima of the smoothed PPG derivative. The beat limit shows the position of the local minima. The signal 440 is the IBI. The signal 442 with squares shows the reference RR intervals (RRI) computed from an ECG signal. The ECG is used as a reference measurement for validating the method. The signal 444 is the beat limit. Asterix 446 indicates a correct beat. The signal 450 is the IB. Asterix 455 indicates a correctly estimated beat with respect to the RRI reference. In this example, there is no motion detected by the acceleration signal and the beat motion level is zero. PPG signal is free of artefacts. The IBI in the example of FIG. 4 matches with the reference measurement.

Figure 5:
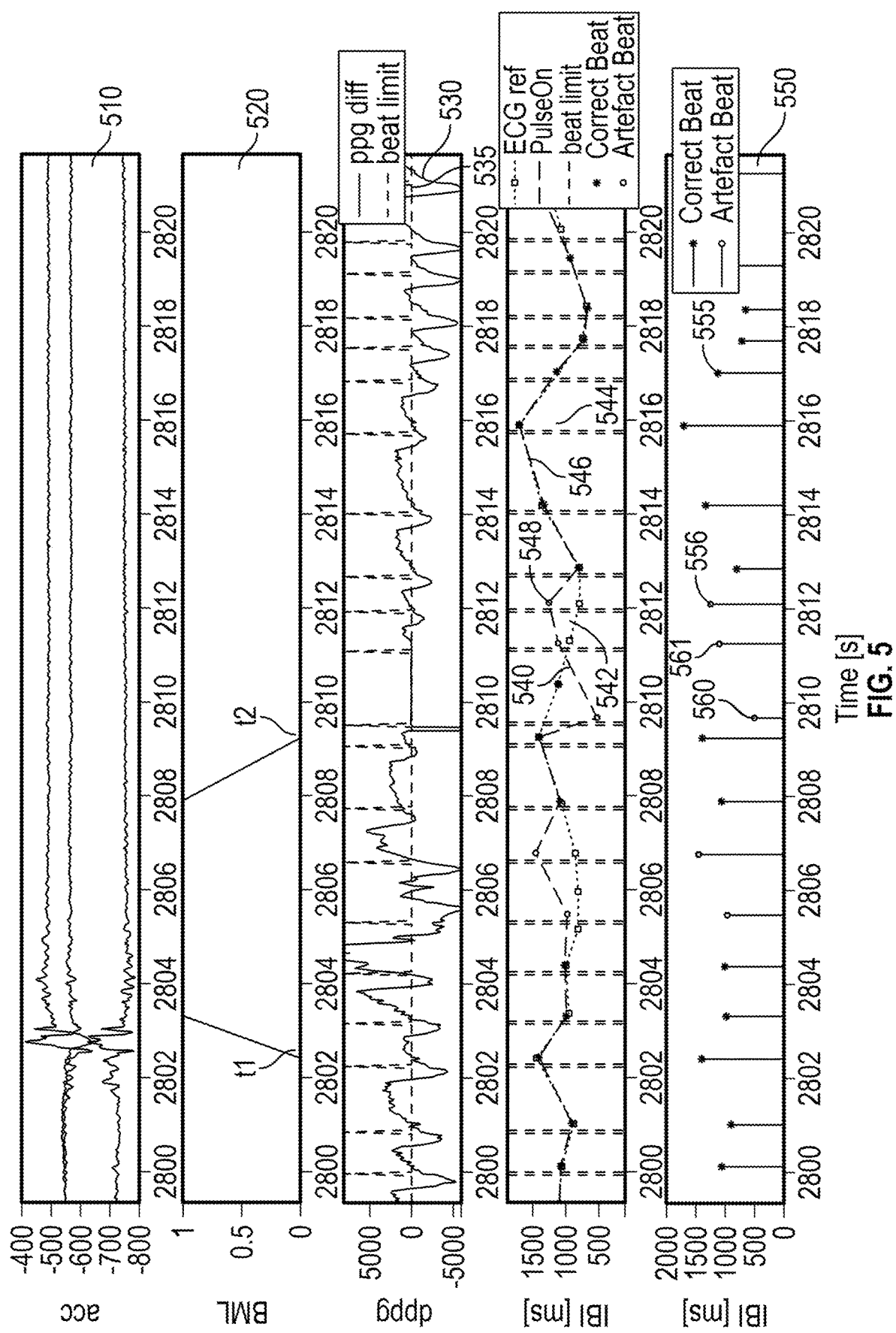
FIG. 5 shows examples of signals.

FIG. 5 shows examples of signals. The signal 510 is the acceleration signal. The signal 520 is the beat motion level. The signal 530 is the derivative of a PPG signal. The signal 535 is the beat limit. The signal 540 is the IBI. The signal 542 with squares shows the reference RR intervals computed from an ECG signal. The ECG is used as a reference measurement for validating the method. The signal 544 is the beat limit. Asterix 546 indicates a correct beat and a circle 548 indicates an artefact with respect to the RRI reference. In the example of FIG. 5, an IBI for which the error with respect to the RRI is higher than 50 ms are considered artefacts. Threshold for the error may be pre-defined as e.g. 45-55 ms, e.g. 47 ms or 52 ms. The signal 550 is the IB. Asterix 555 indicates a correctly estimated beat and a circle 556 indicates an artefact. In this example, motion is detected by the acceleration signal and the beat motion level is above zero between a time interval from t1 to t2. In this interval, the PPG signal is corrupted by motion. The corrupted beats between t1 and t2 are detected by the method disclosed herein, e.g., when the beat motion level is 1. The corrupted beats may be classified as non-reliable and discarded. In the example of FIG. 5, the beat motion level does not detect corrupted beats 560, 561, 556 occurring after t2. To fix this, the beats may be assigned a reliability weight, as described later. Due to a low cross-correlation score, described later, the beats 560, 561, 556 occurring after t2 are classified as non-reliable.

Figure 6:
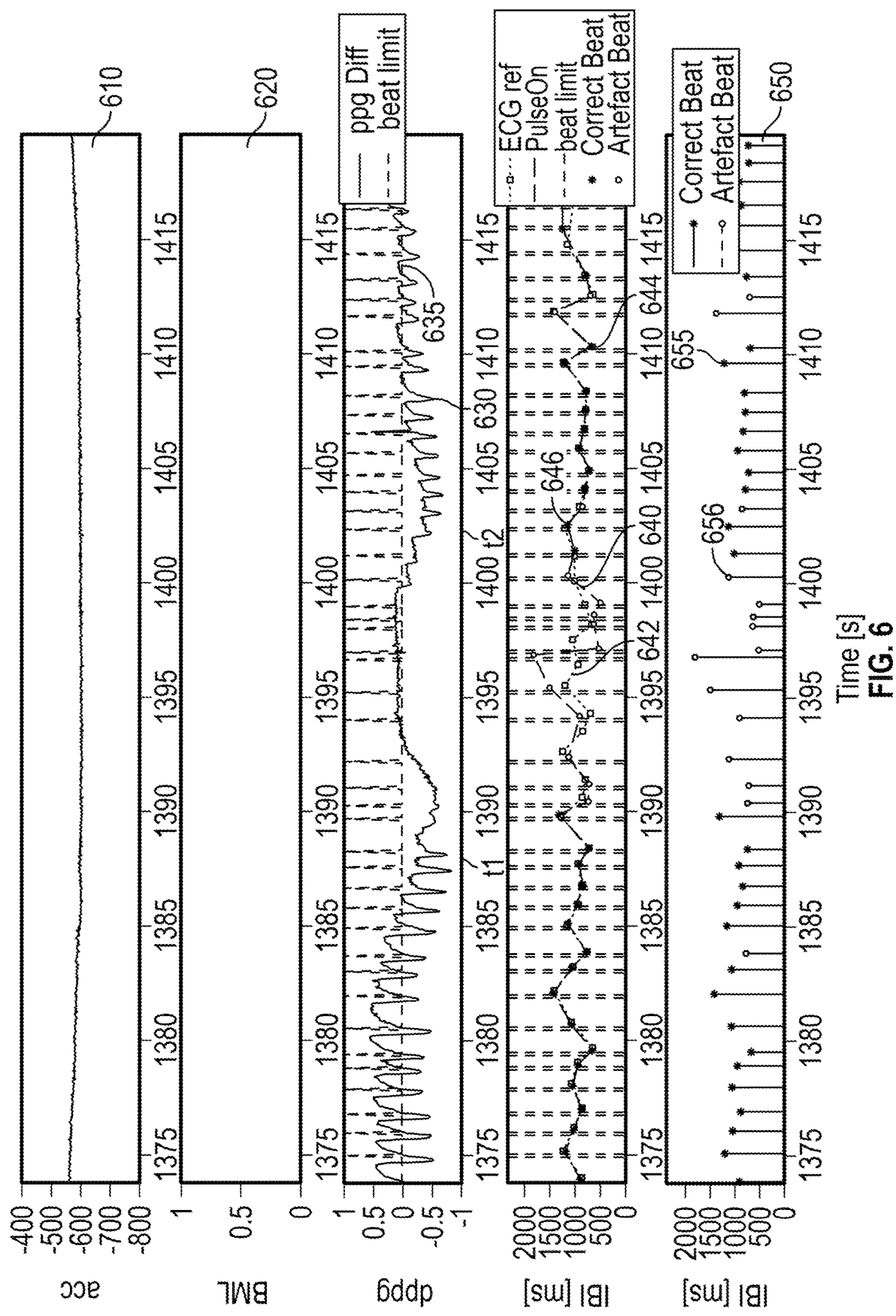
FIG. 6 shows examples of signals.

The PPG signal may be corrupted even though no motion has been detected based on the acceleration signal. FIG. 6 shows examples of signals. The signal 610 is the acceleration signal. The signal 620 is the beat motion level. The signal 630 is the derivative of the PPG signal. The signal 635 is the beat limit. The signal 640 is the IB. The signal 642 shows the reference RR intervals computed from an ECG signal. The ECG is used as a reference measurements for validating the method. The signal 644 is the beat limit. Asterix 646 indicates a correct beat and a circle 648 indicates an artefact with respect to the RRI reference. In the example of FIG. 6, IBI for which the error with respect to the RRI is higher than 50 ms are considered artefacts. Threshold for the error may be pre-defined as e.g. 45-55 ms, e.g. 47 ms or 52 ms. The signal 650 is the IBI. Asterix 655 indicates a correct beat and a circle 656 indicates an artefact. In this example, the dPPG signal is corrupted approximately between a time interval from t1 to t2 even though no motion has been detected based on the acceleration signal. The corrupted beats are detected by the method disclosed herein. The corrupted beats may be classified as non-reliable and may be discarded from further processing.

Figure 7:
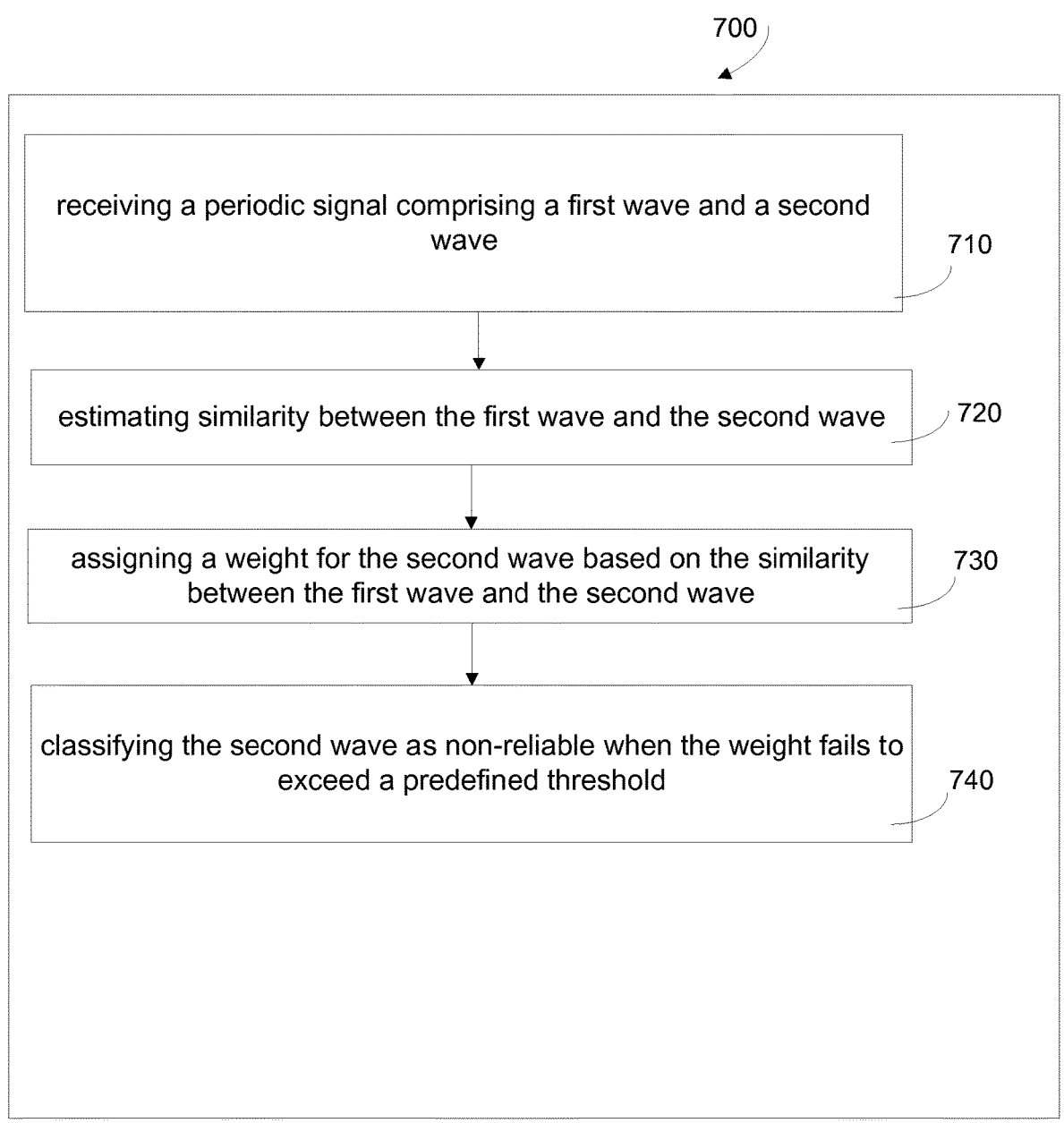
FIG. 7 shows, by way of an example, a flowchart of a method.

Individual assessment of waves of a periodic signal, e.g. PPG waves, may be performed by a method disclosed herein. FIG. 7 shows, by way of an example, a flowchart of a method 700 for estimating quality of a signal. The method comprises receiving 710 a periodic signal comprising a first wave and a second wave. The method comprises estimating 720 similarity between the first wave and the second wave. The method comprises assigning 730 a weight for the second wave based on the similarity between the first wave and the second wave. The method comprises classifying 740 the second wave as non-reliable when the weight fails to exceed a predefined threshold.

According to an embodiment, the first and the second waves are consecutive waves. Using consecutive waves provides for reliable results, fast reaction times, and low memory requirements. Alternatively, there may be e.g. 1, 2, 3 or 4 waves between the first and the second waves, but the reliability of the quality estimation may be reduced.

According to an embodiment, the signal is a PPG signal comprising a first PPG wave and a second PPG wave. A derivative or a filtered derivative of the PPG (dPPG) signal may be determined for further analysis of the signal. Use of the dPPG instead of a raw PPG signal may result in increased accuracy.

According to an embodiment, a corresponding IBI is determined for waves of the PPG signal or for waves of the dPPG Estimating similarity may comprise determining a normalized first wave and a normalized second wave. For each two consecutive waves, w(n) and w(n−1), normalized wave $f_{norm}=(w-mean(w))/std(w))$. Warped versions of the normalized first and the second waves may be determined. Dynamic time warping (DTW) is a pattern matching algorithm with a nonlinear time alignment. DTW is a method that calculates an optimal match between two given sequences, such as the normalized first and the second waves. The first and the second waves may be compared to each other in such a way that a total distance between the two waves, or signals, is minimized. The distance may be an Euclidean distance between points in the wave. Inputs for the DTW may be the derivative or filtered derivative of the PPG signal for each beat. First normalized wave, w(n−1) is considered as a template. DTW nonlinearly stretches the waves, e.g. the second wave w(n), to fit with the template.

Alternatively, the template may be stretched to fit with the wave. When only a single previous pulse is considered as the template, there is no need of prior data or previously validated library templates to carry out signal analysis of the signal. Using the previous pulse as the template provides for easier implementation and better computational efficiency and low memory requirements. The method may be carried out e.g. in the monitoring device without communication connection to an external server. Using the previous pulse provides for fast reaction to changes in signal characteristics or quality.

Alternative methods for DTW are direct matching or linear resampling or pulse feature comparison.

The correlation coefficient, e.g. the cross-correlation coefficient, between the warped versions of the normalized first and the second waves may be determined. If the cross-correlation coefficient is above a predefined threshold, the second wave is classified as reliable. In case of the PPG signal, the second PPG wave and the corresponding IBI are classified as reliable. If the cross-correlation coefficient fails to exceed a predefined threshold, the second wave is classified as non-reliable. In case of the PPG signal, the second PPG wave and the corresponding IBI are classified as non-reliable.

The cross-correlation coefficient may have values between −1 and 1. The morphology of the PPG waves that have high quality should be similar. Thus, the cross-correlation coefficient of the warped versions of good quality waves is high. The threshold for the cross-correlation coefficient may be set to e.g. 0.95. Other examples for the threshold are e.g. 0.94 and 0.96.

The weight, i.e. the reliability weight, can be the cross-correlation coefficient, or may be based on a distance from the predefined threshold. For example, if the cross-correlation coefficient is above the threshold, the weight can be 1; if the cross-correlation coefficient is below the threshold, the weight can be 1 minus a multiple (e.g., 3.5, 4 or 4.5 times) of the distance from the threshold. If the weight is zero or negative, the wave and/or the corresponding computed IBI will be discarded as non-reliable. As an example, if the threshold is 0.95 and the cross-correlation coefficient is 0.97 or 0.99, the weight will be 1. If the threshold is 0.95 and the cross-correlation coefficient is 0.8, the weight will be 1−4× (0.95−0.8)=0.4. Nonlinear relations can also be used. Discarding the non-reliable waves and IBI results an improved signal quality.

It may be possible that the cross-correlation coefficient is high even though motion of the user is present and causes motion artefacts to the PPG signal. If the motion of the user is intense and periodic, consecutive waves may be similar because of a strong periodic motion component in the PPG signal. These false similarities may be detected by the use of the acceleration signal described earlier. If the beat motion level exceeds a predefined threshold, the wave may be classified as non-reliable, even though the cross-correlation coefficient exceeds a predefined threshold.

DTW may be explained by the following example. Suppose we have two time series, T(template) and B(beat) with the length of n and m, respectively. T may be considered as the first wave and the B as the second wave. The lengths need not be equal for DTW. A distance between these two vectors may be evaluated. A distance matrix n×m may be constructed to align the T and B where the $(i,j)^{th}$ element of this matrix contains the distance between the two points $T_i$ and $B_j$ and corresponds to the alignment between the points $T_i$ and $B_j$. Using the Euclidean distance, the distance is $d(T_i, B_j)=((T_i-B_j)^2)$.

The total distance is a sum of distances between aligned vectors. The goal is to find the alignment with the smallest total distance and find an optimal path from (1,1) to (n,m). This may be carried out using the dynamic programming technique, in which the accumulated distance to any grid point (i,j) may be determined recursively. The cumulative distance C(i,j) is defined as the distance d(i,j) found in the current grid point and the minimum of the cumulative distances of the adjacent elements:

$$C(i,j)=d(T_i,B_j)+\min\{C(i-1,j-1),C(i-1,j),C(i,j-1)\}$$

DTW may be determined, for example, by the following algorithm:
Start with the calculation of C(1,1)=d(1,1).
Calculate the first row C(i,1)=d(i,1)+C(i−1,1).
Calculate the first column C(1,j)=d(1,j)+C(1,j−1).
Move to the second row: C(i,2)=d(i,2)+min{C(i,1), C(i−1,1), C(i−1,2)}.
For each cell, keep the index of this neighbouring cell with the minimum score.
Carry on with the rest of the grid: C(i,j)=d(i,j)+min{C(i,j−1), C(i−1,j−1), C(i−1,j)}.
Trace back the best path through the grid starting from C(n,m) and moving towards C(1,1).
The non-normalized DTW distance is Dist=C(n,m).

Let's consider T with length of 7 and B with length of 6, the n-by-m distance matrix d and cumulative distance matrix C:

$$T = [0\ 1\ 1\ 2\ 3\ 2\ 1]\ B = [1\ 1\ 2\ 3\ 2\ 0]$$

$$d = \begin{bmatrix} 1 & 1 & 4 & 9 & 4 & 0 \\ 0 & 0 & 1 & 4 & 1 & 1 \\ 0 & 0 & 1 & 4 & 1 & 1 \\ 1 & 1 & 0 & 1 & 0 & 4 \\ 4 & 4 & 1 & 0 & 1 & 9 \\ 1 & 1 & 0 & 1 & 0 & 4 \\ 0 & 0 & 1 & 4 & 1 & 1 \end{bmatrix} C = \begin{bmatrix} 1 & 2 & 6 & 15 & 19 & 19 \\ 1 & 1 & 2 & 6 & 7 & 8 \\ 1 & 1 & 2 & 6 & 7 & 8 \\ 2 & 2 & 1 & 2 & 2 & 6 \\ 6 & 6 & 2 & 1 & 2 & 11 \\ 7 & 7 & 2 & 2 & 1 & 5 \\ 7 & 7 & 3 & 6 & 2 & 2 \end{bmatrix}$$

Figure 8A:
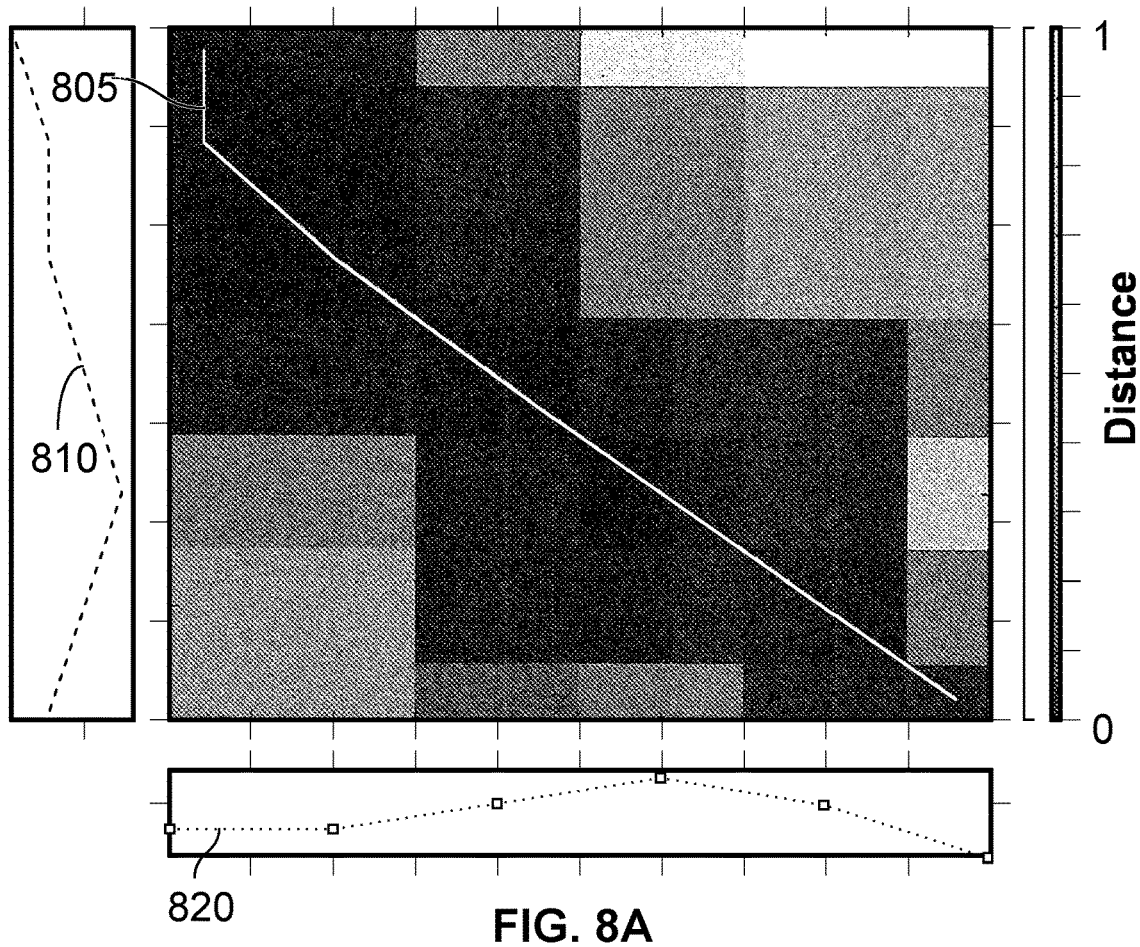
FIG. 8a shows, by way of an example, an optimal path of DTW.
Figure 8B:
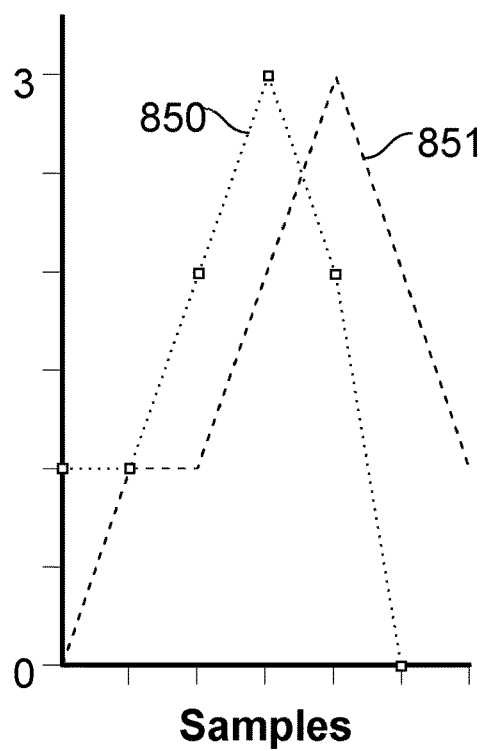
FIG. 8b shows, by way of an example, original signals and warped signals using DTW.
Figure 8B:
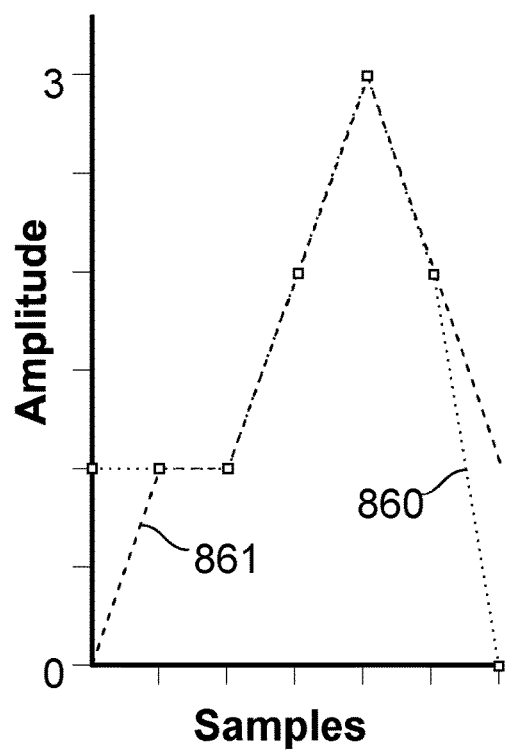

FIG. 8a shows, by way of an example, an optimal path 805 of the DTW. The DTW minimum path in this example is
((1,1), (2,1), (3,2), (4,3), (5,4), (6,5), (7,6)) and the warped signals are wT=[0 1 1 2 3 2 1] and wB=[1 1 1 2 3 2 0]. The curve 810 is the template T and the curve 820 is the beat. FIG. 8b, shows, by way of an example, the original signals 850, 851 and warped signals 860, 861 using DTW. The dotted line 850 and dotted line 860 are the beat signals and the dashed line 851 and dashed line 861 are the template signals.

FIG. 9a shows, by way of an example, original signals 910, 911 and warped signals 920, 921 using DTW. The dotted line 910 and dotted line 920 are the beat signals and the dashed line 911 and dashed line 921 are the template signals. The cross-correlation coefficient in the example of FIG. 9a is high, 0.99.

FIG. 9b shows, by way of an example, original signals 950, 951 and warped signals 960, 961 using DTW. The dotted line 950 and dotted line 960 are the beat signals and the dashed line 951 and dashed line 961 are the template signals. The cross-correlation coefficient in the example of FIG. 9b is low, 0.88. According to an embodiment, the method comprises receiving accelerometer signal. The signal may be received from the accelerometer or from a memory of the apparatus, e.g. the monitoring device. The waves, e.g. PPG waves, may be classified based on the accelerometer signal. Beat motion level may be determined based on the accelerometer signal. If the beat motion level exceeds a predefined threshold, the wave may be classified as non-reliable. One or more beats, e.g. four beats, following the non-reliable wave may also be classified as non-reliable.

An apparatus for estimating the quality of a signal may comprise means for receiving a periodic signal comprising a first wave and a second wave. The apparatus may comprise means for estimating similarity between the first wave and the second wave. The apparatus may comprise means for assigning a weight for the second wave based on the similarity between the first wave and the second wave. The apparatus may comprise means for classifying the second wave as non-reliable when the weight fails to exceed a predefined threshold. The apparatus may comprise means for determining the derivative of the PPG signal. The apparatus may comprise means for determining an inter-beat interval (IBI) for the second PPG wave. The apparatus may comprise means for determining a normalized first wave and a normalized second wave. The apparatus may comprise means for determining warped versions of the normalized first and the second waves. The apparatus may comprise means for determining a correlation coefficient between the warped versions of the normalized first and the second waves. The apparatus may comprise means for classifying the second wave as non-reliable if the correlation coefficient fails to exceed a predefined threshold. The apparatus may comprise means for receiving accelerometer signal. The apparatus may comprise means for classifying the waves based on the accelerometer signal, the classifying comprising determining beat motion level based on the accelerometer signal. The apparatus may comprise means for classifying the waves as non-reliable if the beat motion level exceeds a predefined threshold. The apparatus may comprise means for classifying one or more beats following the non-reliable wave as non-reliable. The apparatus may comprise means for assigning the weight based on a distance of the similarity from the threshold, wherein the weight is obtained by subtracting a multiple of the distance from 1. The apparatus may comprise means for discarding the second wave as non-reliable when the weight is zero or negative.

It is obvious that the present invention is not limited solely to the above-presented embodiments, but it can be modified within the scope of the appended claims.

EXAMPLES

The examples present two situations highlighting the benefits of the signal quality estimation method described herein.

1. Heart Beat Interval Estimation

Photoplethysmographic (PPG) signals were used to measure heart beat intervals, named in the following inter-beat intervals (IBI). These intervals could be further used for heart-rate variability analysis or arrhythmia detection.

IBI estimation from PPG signals is not accurate in the presence of motion or other types of noise. Because heart-rate variability analysis or arrhythmia detection applications are highly sensitive to IBI errors, it is important to filter out unreliable IBI.

The table 1 below shows the mean absolute error (MAE) and mean absolute percentage error (MAPE) for IBI estimation in two situations:
  for all detected IBI (without the proposed signal quality estimation method)
  for reliable IBI (automatically classified as reliable/unreliable by the proposed signal quality estimation method)

The evaluation was done on 494.4 hours of data from 14 recordings; 6 subjects, 4 male, 2 female, 34.6±9.6 years old; 4 out of the 6 subjects had episodic arrhythmias during the measurement.

TABLE 1

| IBI estimation performance | | |
|---|---|---|
| | All IBI | Reliable IBI |
| MAE [ms] | 56.42 | 8.84 |
| MAPE [%] | 7.17 | 0.97 |

Automatically detecting (and not using) unreliable data reduces the MAE from 56.42 ms to 8.84 ms, and the MAPE from 7.17% to 0.97%.

2. Arrhythmia Detection

IBI series were used for detecting arrhythmias, such as atrial fibrillation (AF).

The table 2 below shows the AF detection results in two situations:
  for all detected IBI (without the proposed signal quality estimation method)
  for reliable IBI (automatically classified as reliable/unreliable by the proposed signal quality estimation method)

The evaluation was done on 40 sets with lengths between 4 and 9 hours. The overall duration is 248.3 hours, out of which 64.4 are AF and 183.9 sinus rhythm (SR).

TABLE 2

| AF/SR classification results | | | | |
|---|---|---|---|---|
| | | SR [%] | AF [%] | Classified intervals [%] |
| All IBI | SR | 81.98 | 18.02 | 100 |
| | AF | 3.14 | 96.86 | |
| Reliable IBI | SR | 99.72 | 0.28 | 66.20 |
| | AF | 1.80 | 98.20 | |

Both the sensitivity (true positive rate) and specificity (true negative rate) increase when applying the signal quality estimation method. The sensitivity increases from 96.86% to 98.20%, and the specificity from 81.98% to 99.72%. When the input data is not reliable, the output will also not be classified, but this is preferred to taking a wrong decision.

The invention claimed is:

1. A method for estimating the quality of a photoplethysmogram (PPG) signal comprising:
  receiving a PPG signal from an optical sensor;
  determining a derivative of the PPG signal, wherein the derivative of the PPG signal comprises a first PPG wave and second PPG wave;
  estimating similarity between the first PPG wave and the second PPG wave of the determined derivative of the PPG signal, wherein the first and the second PPG waves are consecutive waves of the determined derivative of the PPG signal;
  assigning a weight for the second PPG wave based on the similarity between the first PPG wave and the second PPG wave; and
  discarding the second PPG wave based on the weight failing to exceed a predefined threshold; and
  producing a filtered PPG signal based at least in part on the derivative of the PPG signal without the discarded second PPG wave.

2. The method according to claim 1, further comprising determining an inter-beat interval (IBI) for the second PPG wave.

3. The method according to claim 1, wherein estimating similarity comprises
  determining a normalized first PPG wave and a normalized second PPG wave;
  determining warped versions of the normalized first and the second PPG waves;
  determining a correlation coefficient between the warped versions of the normalized first and the second PPG waves; and
  classifying the second PPG wave as non-reliable if the correlation coefficient fails to exceed a predefined threshold.

4. The method according to claim 1, further comprising
  receiving accelerometer signal;
  classifying the PPG waves based on the accelerometer signal, the classifying comprising determining beat motion level based on the accelerometer signal; and
  classifying the PPG waves as non-reliable if the beat motion level exceeds a predefined threshold.

5. The method according to claim 4, further comprising classifying one or more beats following the non-reliable wave as non-reliable.

6. The method according to claim 1, further comprising assigning the weight based on a distance of the similarity from the threshold, wherein the weight is obtained by subtracting a multiple of the distance from 1.

7. The method according to claim 1, further comprising discarding the second PPG wave as non-reliable when the weight is zero or negative.

8. An apparatus comprising at least one processor; at least one memory including computer program code; and the at least one memory and the computer program code are configured, with the at least one processor, to:
  receive a PPG signal from an optical sensor;
  determine a derivative of the PPG signal, wherein the derivative of the PPG signal comprises a first PPG wave and a second PPG wave;
  estimate similarity between the first PPG wave and the second PPG wave of the determined derivative of the PPG signal, wherein the first and the second PPG waves are consecutive waves of the determined derivative of the PPG signal;
  assign a weight for the second PPG wave based on the similarity between the first PPG wave and the second PPG wave;
  discard the second PPG wave based on the weight failing to exceed a predefined threshold; and
  produce a filtered PPG signal based at least in part on the derivative of the PPG signal without the discarded second PPG wave.

9. The apparatus according to claim 8, wherein the apparatus is a monitoring device comprising an optical sensor for measuring photoplethysmogram (PPG) signals.

10. The apparatus according to claim 8, wherein the apparatus is a portable and/or wearable biometric monitor.

11. The apparatus according to claim 8 wherein the means comprises at least one processor; at least one memory including computer program code; the at least one memory and the computer program code configured to, with the at least one processor, cause the performance of the apparatus.

12. The apparatus according to claim 8, wherein the at least one memory and the computer program code are configured, with the at least one processor, to determine an inter-beat interval (IBI) for the second PPG wave.

13. The apparatus according to claim 8, wherein the at least one memory and the computer program code are configured, with the at least one processor, to estimate similarity by:
- determining a normalized first PPG wave and a normalized second PPG wave;
- determining warped versions of the normalized first and the second PPG waves;
- determining a correlation coefficient between the warped versions of the normalized first and the second PPG waves; and
- classifying the second PPG wave as non-reliable if the correlation coefficient fails to exceed a predefined threshold.

14. The apparatus according to claim 8, wherein the at least one memory and the computer program code are configured, with the at least one processor, to: receive accelerometer signal; classify the PPG waves based on the accelerometer signal by: determining beat motion level based on the accelerometer signal; and classifying the PPG waves as non-reliable if the beat motion level exceeds a predefined threshold.

15. The apparatus according to claim 14, wherein the at least one memory and the computer program code are configured, with the at least one processor, to classify one or more beats following the non-reliable wave as non-reliable.

16. The apparatus according to claim 8, wherein the at least one memory and the computer program code are configured, with the at least one processor, to assign the weight based on a distance of the similarity from the threshold, wherein the weight is obtained by subtracting a multiple of the distance from 1.

17. The apparatus according to claim 8, wherein the at least one memory and the computer program code are configured, with the at least one processor, to discard the second PPG wave as non-reliable when the weight is zero or negative.

18. A non-transitory computer-readable medium storing a computer program comprising computer program code configured to, when executed on at least one processor, cause an apparatus to carry out a method for estimating the quality of a photoplethysmogram (PPG) signal, the method comprising:
- receiving a PPG signal from an optical sensor;
- determining a derivative of the PPG signal, wherein the derivative of the PPG signal comprises a first PPG wave and a second PPG wave;
- estimating similarity between the first PPG wave and the second PPG wave of the determined derivative of the PPG signal, wherein the first and the second PPG waves are consecutive waves of the determined derivative of the PPG signal;
- assigning a weight for the second PPG wave based on the similarity between the first PPG wave and the second PPG wave;
- discarding the second PPG wave based on the weight failing to exceed a predefined threshold; and
- producing a filtered PPG signal based at least in part on the derivative of the PPG signal without the discarded second PPG wave.

* * * * *